(12) United States Patent
Kovi et al.

(10) Patent No.: US 9,150,511 B2
(45) Date of Patent: Oct. 6, 2015

(54) PROCESS FOR PREPARING SAXAGLIPTIN AND ITS NOVEL INTERMEDIATES USEFUL IN THE SYNTHESIS THEREOF

(71) Applicant: Apicore US LLC, Somerset, NJ (US)

(72) Inventors: Ravishanker Kovi, Monroe, NJ (US); KeshavRao Rapole, Edison, NJ (US); Ashish Naik, Piscataway, NJ (US); Jayaraman Kannapan, Gujrat (IN); Muralikrishna Madala, Andhra Pradesh (IN); Sanjay Thakor, Gujarat (IN)

(73) Assignee: Apicore US LLC, Somerset, NJ (US)

( * ) Notice: Subject to any disclaimer, the term of this patent is extended or adjusted under 35 U.S.C. 154(b) by 0 days.

(21) Appl. No.: 14/264,770

(22) Filed: Apr. 29, 2014

(65) Prior Publication Data

US 2014/0235870 A1 Aug. 21, 2014

Related U.S. Application Data

(62) Division of application No. 13/479,975, filed on May 24, 2012, now Pat. No. 8,748,631.

(60) Provisional application No. 61/489,478, filed on May 24, 2011.

(51) Int. Cl.
| | |
|---|---|
| *A01N 43/38* | (2006.01) |
| *A61K 31/40* | (2006.01) |
| *C07D 209/52* | (2006.01) |
| *C07D 209/48* | (2006.01) |
| *C07C 29/147* | (2006.01) |
| *C07C 67/11* | (2006.01) |
| *C07C 45/30* | (2006.01) |
| *C07D 403/06* | (2006.01) |

(52) U.S. Cl.
CPC ............ *C07D 209/48* (2013.01); *C07C 29/147* (2013.01); *C07C 45/30* (2013.01); *C07C 67/11* (2013.01); *C07D 209/52* (2013.01); *C07D 403/06* (2013.01); *C07C 2103/74* (2013.01)

(58) Field of Classification Search
CPC .................................................... C07D 209/52
USPC .................................................. 548/452, 455
See application file for complete search history.

(56) References Cited

U.S. PATENT DOCUMENTS

| | | | |
|---|---|---|---|
| 7,420,079 | B2 | 9/2008 | Vu et al. |
| 2003/0219880 | A1 | 11/2003 | Ouazzani et al. |
| 2005/0090539 | A1 | 4/2005 | Vu |
| 2006/0035954 | A1 | 2/2006 | Sharma |
| 2008/0045477 | A1 | 2/2008 | Antoniadou-Vyza et al. |
| 2008/0161563 | A1 | 7/2008 | Topping et al. |
| 2010/0274025 | A1 | 10/2010 | Vu |
| 2010/0291020 | A1 | 11/2010 | Arora et al. |

OTHER PUBLICATIONS

Franklin A. Davis, et al., Masked Oxo Sulfinimines (N-Sulfinyl-Imines) in the Asymmetric Synthesis of Proline and Pipecolic Acid Derivatives, American Chemical Society, Organic Letters. vol. 3, No. 5, pp. 759-762 (2001).
Phillip M. Weintraub, et al., Recent advances in the synthesis of piperidones and piperidines, Science Direct, Tetrahedron 59 pp. 2953-2989 (2003).
International Search Report and Written Opinion for corresponding PCT Application PCT/US2012/39353, dated Aug. 17, 2012.
Lyzwa et al., Asymetric Synthesis of aminophosphonic acids mediated by chiral suflinyl auxiliary: Recent advances. Pure Appl. Chem., vol. 82, No. 3, pp. 577-582; available at: http://stage.iupac.org/publications/pac/pdf/2010/pdf/8203x0577.pdf, 2010.
Santosh K. Singh, et al., Synthesis of (S)-1-(2-chloroacetyl)pyrrolidine-2-carbonitrile: A key intermediate for dipeptidyl peptidase IV inhibitors, Beilstein Journal of Organic Chemistry, 4, No. 20 (2008).
Scott A. Savage, et al., Preparation of Saxagliptin, a Novel DPP-IV Inhibitor, Organic Process Research & Development, vol. 13, No. 6, pp. 1169-1176 (2009).
D. J. Augeri et al.: "Discovery and Preclinical Profile of Saxagliptin (BMS-477118): A Highly Potent, Long-Acting, Orally Active Dipeptidyl Peptidase IV Inhibitor for the Treatment of Type 2 Diabetes.", Journal of the American Chemical Society, pp. 5025-5037, vol. 48, No. 15, (Jun. 24, 2005).
S. A. Savage et al.: "Preparation of Saxagliptin, a Novel DPP-IV Inhibitor.", Organic Process Research and Development, vol. 13, pp. 1169-1176 (Oct. 16, 2009).
P. Cole et al.: "Saxagliptin", Drugs of the Future, vol. 33, No. 7, pp. 577-586, (Jul. 1, 2008).
Supplementary Partial European Search Report for corresponding EP Application No. 12788759, dated Feb. 16, 2015.

*Primary Examiner* — Nyeemah A Grazier

(74) *Attorney, Agent, or Firm* — Timothy X. Gibson, Esq.; Gibson & Dernier LLP

(57) ABSTRACT

Methods of making saxagliptin, pharmaceutically acceptable salts and hydrates thereof and intermediates thereof.

2 Claims, No Drawings

PROCESS FOR PREPARING SAXAGLIPTIN AND ITS NOVEL INTERMEDIATES USEFUL IN THE SYNTHESIS THEREOF

CROSS-REFERENCE TO RELATED APPLICATIONS

This application claims priority to and is a divisional of U.S. patent application Ser. No. 13/479,975 filed May 24, 2012, which claims the benefit of U.S. Provisional Patent Application 61/489,478 filed May 24, 2011, the entireties of which are incorporated herein by reference.

FIELD OF THE INVENTION

The present subject matter relates to methods of making saxagliptin, pharmaceutically acceptable salts and hydrates thereof and intermediates thereof.

BACKGROUND OF THE INVENTION

Saxagliptin is a dipeptidyl peptidase (DPP) IV inhibitor useful in the treatment of diabetes. Saxagliptin is understood to slow the breakdown of incretin hormones, thereby increasing the levels of these hormones in the body, which in turn increases the production of insulin in response to meals and decreases the amount of glucose produced by the liver.

SUMMARY OF THE INVENTION

In accordance with the present disclosure, processes for the manufacture of saxagliptin, intermediates and derivatives thereof, are provided which include in one embodiment two amino acid derivatives (A) and (B), described in further detail hereinbelow, coupled in the presence of a coupling reagent. The amide coupling of (S)-α[[(1,1-dimethyleethoxy)carbonyl]amino]-3-hydroxytricyclo[3.3.1.1]decane-1-acetic acid (A) and (1S,3S,5S)-2-azabicyclo[3.1.0]hexane-3-carboxamide (B), subsequent dehydration of the primary amide and deprotection of the amine affords saxagliptin (C).

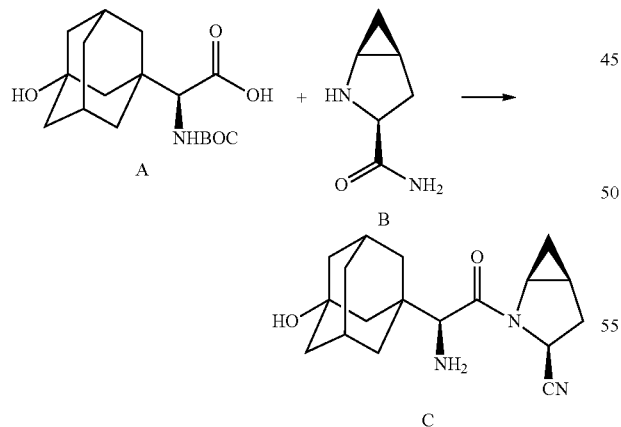

In further embodiments, also provided are methods for asymmetric reductive amination of the intermediate compound (S)-amino-(3-hydroxy-adamantan-1-yl)-acetic acid used in the production of cyclopropyl-fused pyrrolidine-based inhibitors of dipeptidyl peptidase IV. Additional intermediate compounds and methods for their production are also provided. DPP IV inhibitors, pharmaceutically acceptable salts and solvates thereof, produced using the compounds and methods disclosed herein are useful in the treatment of diabetes and complications thereof, hyperglycemia, Syndrome X, hyperinsulinemia, obesity, and atherosclerosis and related diseases, as well as immunomodulatory diseases and chronic inflammatory bowel disease.

In accordance with one embodiment, a method for making saxagliptin hydrochloride monohydrate includes combining (S)-(+)-p-toluenesulfinamide Ti(OEt)$_4$ and adamantane 1-carboxaldehyde to obtain

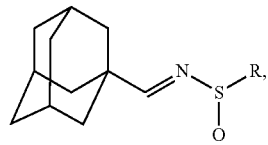

XIX wherein R is alkyl or aryl, treating the resulting compound with NaCN, KCN, trimethylsilyl cyanide (TMSCN) or Et$_2$AlCN and (S)-(+)-p-toluenesulfonamide/Ti(OEt)$_4$ to obtain

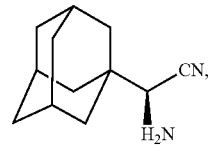

XX treating the resulting compound with phthalic anhydride to obtain

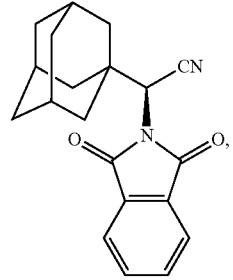

XXI treating the resulting compound with acid to obtain

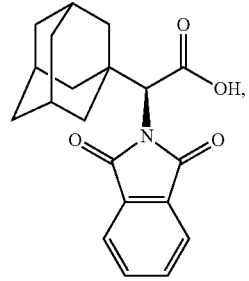

XVIII treating the resulting compound with KMnO₄ to obtain

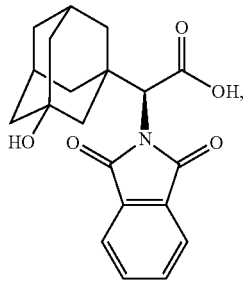

IIIA coupling the resulting compound with methanoproline nitrile using hydroxybenzotriazole (HOBT), 1-ethyl-3-[3-dimethylaminopropyl]carbodiimide hydrochloride (EDC HCl) or N,N-diisopropylethylamine (DIPEA) to obtain

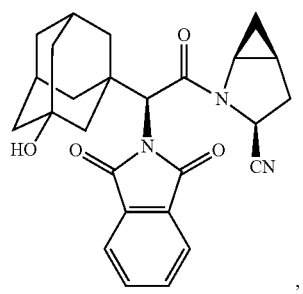

XXII

, and treating the resulting compound with methyl amine and hydrochloric acid.

In accordance with another embodiment, a method is disclosed for making

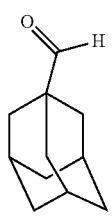

XV which includes the steps of treating adamantane 1-carboxylic acid with dimethyl sulfide and potassium carbonate to obtain

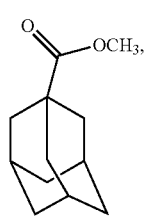

XIII treating the resulting compound with a reducing agent to obtain

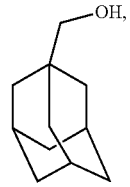

XIV and treating the resulting compound with triethylamine, dichloromethane, and oxalylchloride.

In one embodiment the reducing agent is sodium dihydrobis-methoxyethoxy aluminate solution in toluene.

In yet another embodiment a method for making

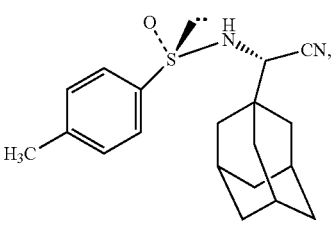

XVIII is disclosed which includes the steps of combining adamantane 1-carboxaldehyde with (S)-(+)-p-toluenesulfinamide using NaCN, NaHSO₃ and potassium permanganate to obtain

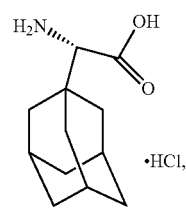

XVI treating the resulting compound with acid to obtain

XVII and treating the resulting compound with dimethylformamide, potassium carbonate and phthalic anhydride.

DETAILED DESCRIPTION

In the following description, for purposes of explanation, specific numbers, materials and configurations are set forth in order to provide a thorough understanding of the invention. It will be apparent, however, to one having ordinary skill in the art that the invention may be practiced without these specific details. In some instances, well-known features may be omitted or simplified so as not to obscure the present invention. Furthermore, reference in the specification to phrases such as "one embodiment" or "an embodiment" means that a particular feature, structure or characteristic described in connection with the embodiment is included in at least one embodiment of the invention. The appearances of phrases such as "in one embodiment" in various places in the specification are not necessarily all referring to the same embodiment.

The presently disclosed subject matter includes a compound I represented below

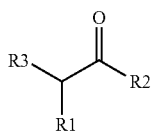

wherein R1 is NH$_2$ or NHR4, wherein R4 is selected from 9-fluorenylmethoxycarbonyl (Fmoc), t-butoxycarbonyl (BOC), alkyl, C1-C5, acetyl (Ac), aryl, Ar=phenyl, benzyl, benzyloxycarbonyl (Cbz), heterocycles, substituted aryl at o, m, p, positions, and

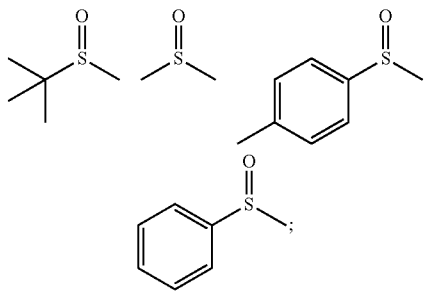

wherein R2 is hydroxy, C1-C8 alkoxy, —NR'R", wherein R' and R" are independently selected from hydrogen, C1-C8 alkyl groups, aryl, benzyl, benzyloxycarbonyl (Cbz) and substituted aryl at o, m, p and oo', pp', mm' positions; and R2 may also be (1S,3S,5S)-2-azabicyclo[3.1.0]hexane-3-nitrile;

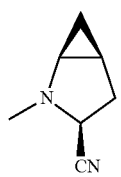

wherein R3 is adamantyl, substituted adamantyl, an alkyl or aryl groups, and adamantyl is

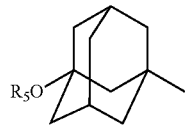

wherein R5 is selected from hydrogen, C1-C5 alkyl, benzoyl, trimethylsilyl (TMS), t-butyldimethylsilyl (TBDMS), acetyl (Ac), p-toluene sulfonyl (Pts), and mesyl (Ms).

In accordance with an embodiment a compound II is represented below

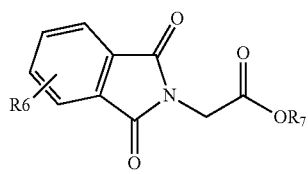

wherein,

R6 is hydrogen at C1-C4, alkyl at C1-C4 (methyl, ethyl, methoxy), or a halogen group (X) at C1-C4 (X=F, Cl, Br, I), and R7 is hydrogen or a C1-C8 alkyl group.

The product of the adamantylation on compound II yields a compound III, represented below. Subsequent cleavage of the phthaloyl group by reaction with hydrazine hydrate followed by hydrolysis of an ester group affords deprotected moiety A of saxagliptin (compound IV, represented below).

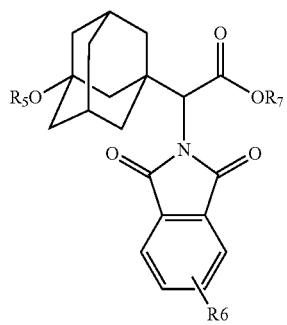

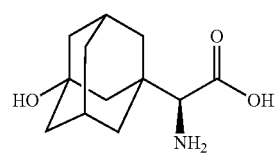

In the compound III represented above, R5, R6, R7 are as defined hereinabove.

The compound II can be synthesized by different methods starting from the compound V or VI as represented below

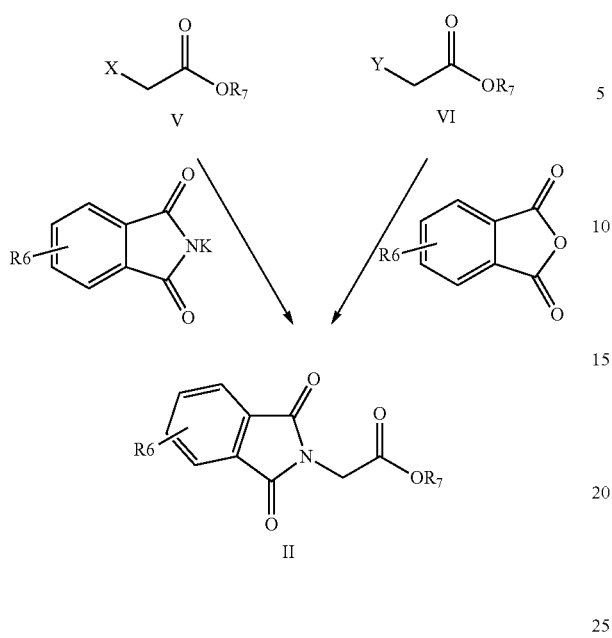

wherein in compound V, R7 is hydrogen or a C1-C8 alkyl group;

X is a halogen such as F, Cl, Br, I; and wherein in compound VI, Y is an amino group (NH$_2$).

The compound II can be synthesized by using a well-known method such as Gabriel synthesis for the phthaloyl protection of amines. The Gabriel synthesis of a-halo acid or ester (V) with potassium phthalimide produces compound (II).

The compound (II) may also be derived through the reaction of glycine methyl ester (VI) with phthalic anhydride.

Scheme-I

In one embodiment a synthetic route is dislosed as follows:

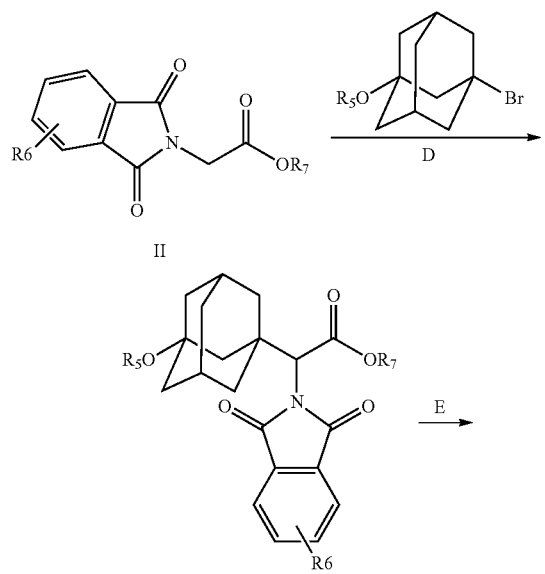

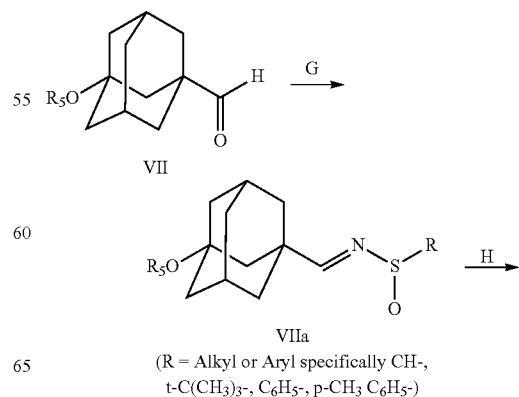

wherein D is, NaH, KH, LiHMDS or NaHMDS;

E is hydrolysis;

F is hydrazine hydrate and

J is a coupling reagent.

The target material represented by C (Scheme-I) can be prepared by reaction with N-pththaloyl glycine ester with base-catalyzed alkylation (adamantyl) followed by hydrolysis to provide compound IIIA, which is further coupled with methanoproline nitrile as amide linkage, and subsequently deprotection of the phthaloyl group to achieve product C.

The base used for the base-catalyzed adamantylation of compound II may be chosen from sodium hydride, lithium hexamethyldisilazide, sodium hexamethyldisilazide and potassium hexamethyl disilazide. In one embodiment lithium hexamethyldisilazide in a solvent such as tetrahydrofuran, dioxane, or aromatic solvents such as toluene is employed. The solvent tetrahydrofuran may be preferred when lithium hexamethyldisilazide is employed.

Scheme -II

In accordance with another embodiment a synthetic route is disclosed as follows:

(R = Alkyl or Aryl specifically CH-, t-C(CH$_3$)$_3$-, C$_6$H$_5$-, p-CH$_3$ C$_6$H$_5$-)

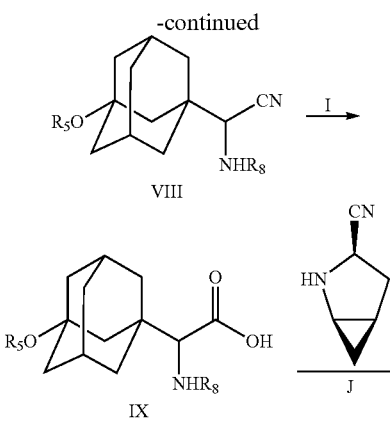

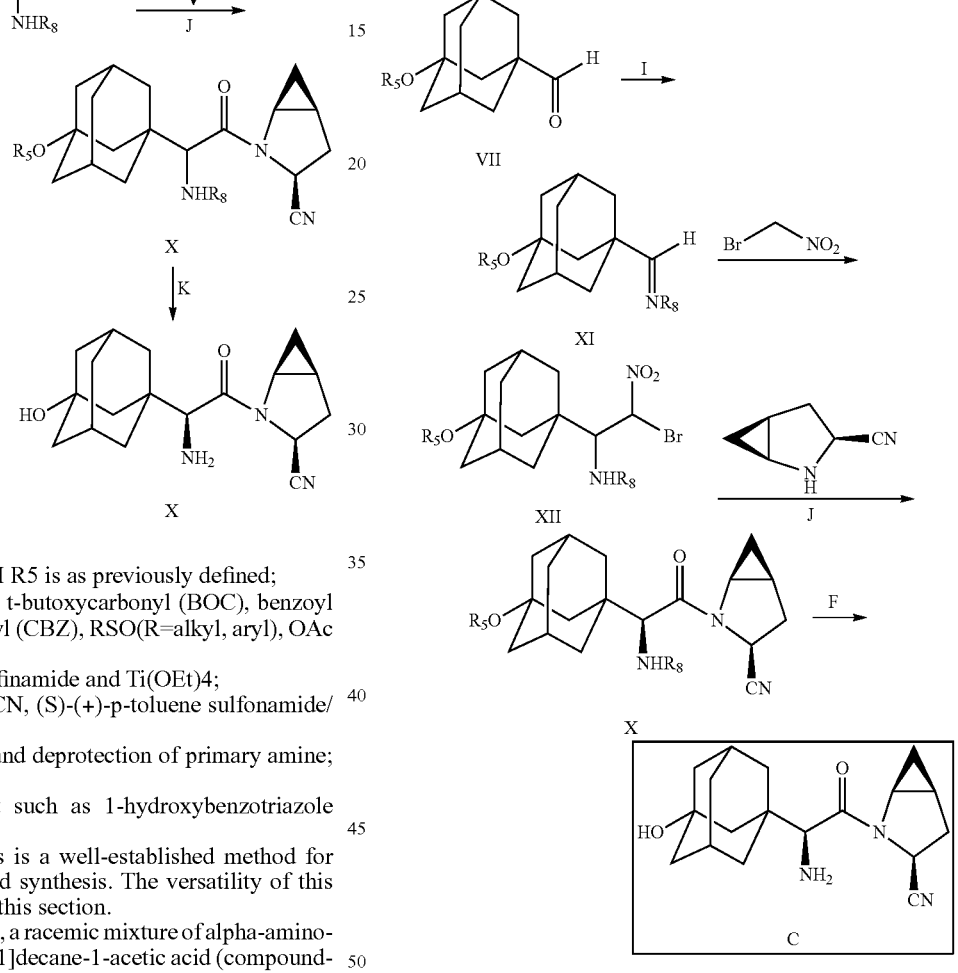

removes the N-sulfinyl auxiliary and converts the nitrile to the acid to provide the chirally pure (S)-α-amino-3-hydroxytricyclo[3.3.1.1]decane-1-acetic acid as depicted in compound IX, which may be further coupled with methanoproline nitrile in the presence of a coupling reagent such as hydroxybenzotriazole (HOBT) followed by hydrolysis to afford the target compound C.

Scheme-III

In accordance with another embodiment a synthetic route is dislosed as follows:

wherein in compound VII R5 is as previously defined;
in compound-VIII, R8 is t-butoxycarbonyl (BOC), benzoyl (BZ), benzoyloxycarbonyl (CBZ), RSO(R=alkyl, aryl), OAc or C1-C8 alkyl;
G is (S)-(+)-p-toluenesulfinamide and Ti(OEt)4;
H is NaCN, KCN, TMSCN, (S)-(+)-p-toluene sulfonamide/ Ti(OEt)$_4$ or Et$_2$AlCN;
I is hydrolysis of nitrile and deprotection of primary amine; and
J is a coupling reagent such as 1-hydroxybenzotriazole (HOBT).

The Strecker synthesis is a well-established method for preparation of amino acid synthesis. The versatility of this process is highlighted in this section.

As shown in Scheme-II, a racemic mixture of alpha-amino-3-hydroxy tricycle[3.3.1.1]decane-1-acetic acid (compound-IX) can be synthesized as per the available literature by chemically starting from tricycle[3.31.1]decane-1-formaldehyde (compound-VII) condensation with sodium cyanide and amine, which is further coupled with methanoproline nitrile in the presence of a coupling reagent followed by hydrolysis to afford target compound C.

However the subject matter represented by compound IV can be synthesized chemically and stereospecifically pure by the following chemical reactions. The adamantyl aldehyde (compound VII) can be converted readily to sulfinime (compound-VIIa) using titanium ethoxide ([Ti(OEt)$_4$) and (S)-p-toluenesulfinamide or similar sulfinamide derivatives followed by a sulfinimine-mediated asymmetric Strecker synthesis using ethyl-aluminium cyanoisopropoxide.

The sulfinyl group controls the stereochemistry of cyanide addition and the corresponding amino nitrile produced (compound-VIII) is predicted to have the (S—S)-configuration. Hydrolysis of the diastereochemically pure amino nitrile wherein in compound XI R8 is t-butoxycarbonyl (BOC), benzoyl (BZ), benzoyloxycarbonyl(CBZ), RSO(R=alkyl, aryl), or C1-C8 alkyl;
I is a base such as Et$_3$N, Na$_2$CO$_3$, or K$_2$CO$_3$,
J is as described above, and
F is hydrolysis, deprotection of amine and OH groups.

In Scheme-III, an efficient route to prepare saxagliptin in four steps is disclosed, starting from 3-hydroxy adamantyl formaldehyde reaction with a primary amine providing a Schiff base (XI), and conversion to imine addition of a bromonitro methane derivative (XII) accomplished through the treatment with bromonitro methane, and finally coupling of the resulting intermediate (X) with methanoproline nitrile that underwent Nef rearrangement to afford a target material as saxagliptin (C).

Example 0

In a clean dry 5 L RB flask equipped with mechanical stirrer, one mole of 3-hydroxy adamantyl formaldehyde is charged along with 1 mole of (S)-(+)-p-toluene sulfinamide, 5 equiv of Ti(OEt)$_4$ in dichloromethane at room temperature to give the compound VIIa.

Example 1

Adamantane-1-aminonitrile

The sulfinimine-mediated asymmetric synthesis involves addition of ethylaluminium cyanoisopropoxide generated in situ by addition of isopropanol (i-PrOH) to diethylaluminium cyanide (Et$_2$AlCN) to the compound VIIa. Thus treatment of compound VIIa (1.0 mmol) at −78° C. in THF with 1.5/1.0 equiv of Et$_2$AlCN/i-PrOH gave amino nitrile VIII in good yield (50-70%).

Example 2

Adamantane amino acid derivative

Into a dry 3 L RB flask equipped with mechanical stirrer were taken a mixture of adamantane-aminonitrile (VIII) (100 g), conc. HCl (2 L) and acetic acid (500 ml). The reaction mixture was stirred at 80-85° C. for 18 hrs. After completion of the reaction, the solvent was distilled out up to ¾ volumes of reaction mass at 90° C. under vacuum. The mixture was cooled to RT, further cooled to 0-5° C. and this temperature was maintained for 2 hrs and then the reaction mass filtered, the solid material was washed with chilled water and dried under vacuum at 70 to 80° C. to afford 55 g of product (adamantane amino acid derivative, IX).

Example 3

(S)-Adamantylglycine derivative

Into a dry autoclave were taken mixture of adamantane amino acid derivative (IX) (100 g), methanol (960 ml) and Pd/C (20 g), the container was flushed with N$_2$ gas twice then H$_2$ gas applied at about 10-15 psi pressure at 25 to 30° C. for 24 hrs. After completion of the reaction, the reaction mixture was filtered through the celite bed, the bed was washed with methanol very thoroughly, and the methanol was distilled out completely under vacuum at 40° C. bath temperature, dried in vacuum to yield about 55 gm of product (S)-adamantylglycine derivative.

Example 4

Coupling reaction to produce 3-cyano (S)-(3-hydroxytricyclo[3.3.1.1]dec-1-yl)oxo-1S,3S,5S)-2-azabicyclo[3.1.0]hexane-2-ethanocarbamic acid, 1,1-dimethylethyl ester A 2 L three-necked flask equipped with a thermometer, a mechanical stirrer and a gas inlet was charged with (S)-a[(ter-butyl sulfinyl)amino]-3-hydroxytricyclo[3.3.1.1]decane-1-acetic acid (50 g). THF (200 ml) was added and stirred to produce a clear solution. The solution was cooled to −6° C. in an acetone-dry ice bath. Methanesulfonyl chloride (13.1 ml) was then added as a single portion followed by addition of diisopropylethylamine (94 ml) slowly over a period of 5 minutes to keep the internal temperature below 0° C. The reaction mixture was stirred at 0° C. until all acid was converted to mixed anhydride. (1S,3S,5S)-2-azabicyclo[3.1.0]hexane-3-carboxamide hydrochloride salt (32.5 g) and hydroxybenzotriazole (HOBT) (1.04 g) were then added in a single portion and the flask was removed from the cooling. The reaction mixture was stirred at room temperature for 2 hrs and then left overnight at room temperature. Product was isolated by traditional work up.

Scheme-IV

In accordance with a further embodiment, a synthetic route is disclosed as follows:

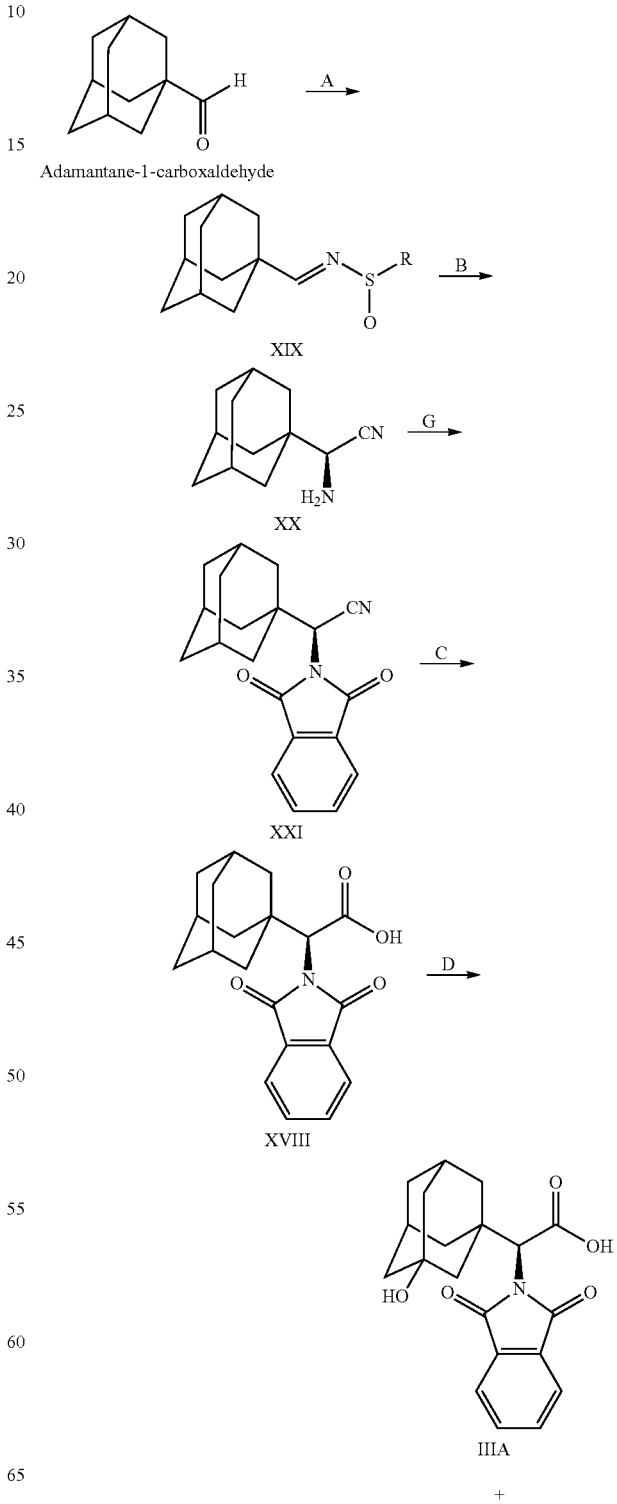

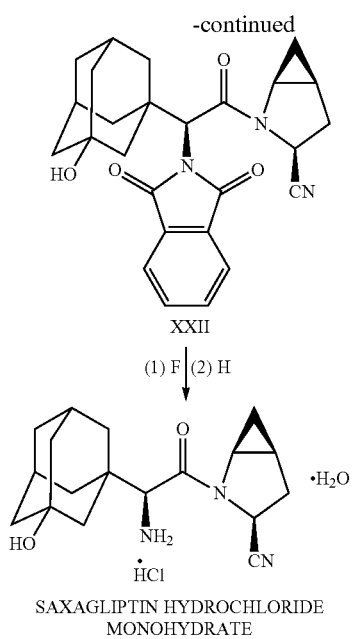

XXII (1) F | (2) H

SAXAGLIPTIN HYDROCHLORIDE
MONOHYDRATE wherein
A is (S)-(+)-p-toluenesulfinamide and Ti(OEt)$_4$;
B is NaCN, KCN, trimethylsilyl cyanide (TMSCN), (S)-(+)-p-toluenesulfonamide/Ti(OEt)$_4$ or Et$_2$AlCN;
C is concentrated Hydrochloric acid and Acetic acid;
D is KMnO$_4$;
E is HOBT, 1-ethyl-3-[3-dimethylaminopropyl]carbodiimide hydrochloride (EDC HCl) or N,N-diisopropylethylamine (DIPEA);
F is methyl amine;
G is phthalic anhydride; and H is concentrated hydrochloric acid;
and wherein in compound XIX R is alkyl or aryl.

Scheme-V
In accordance with a further embodiment, a synthetic route is disclosed as follows:

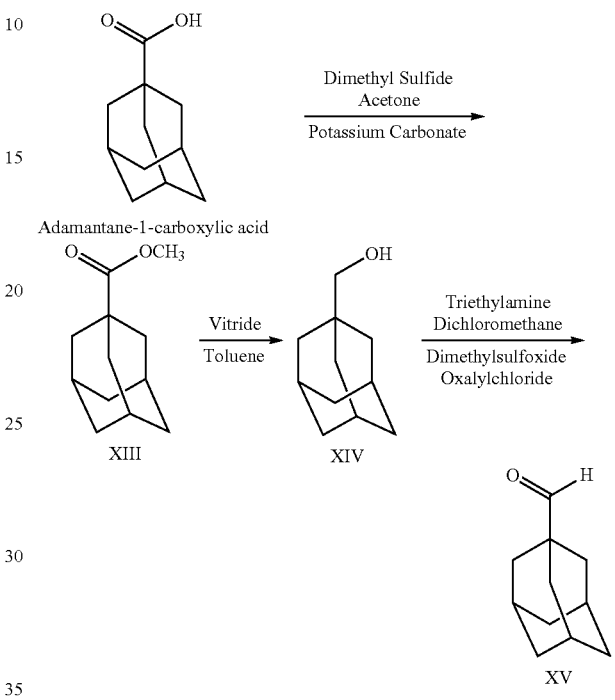

Scheme-VI
In accordance with a further embodiment, a synthetic route is disclosed as follows:

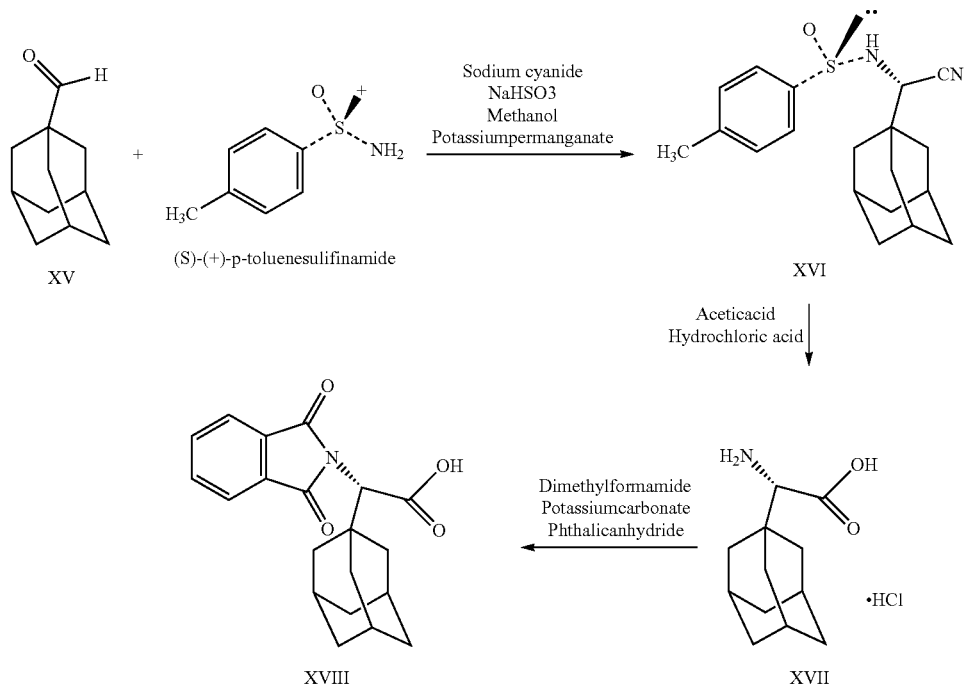

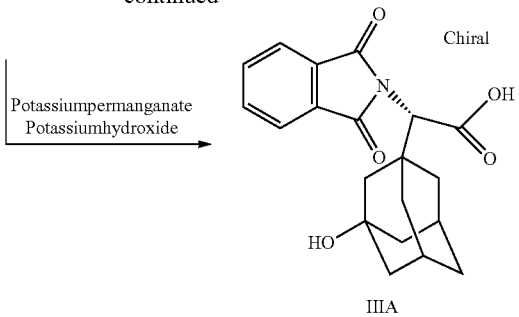

IIIA

Example-5

Charge adamantane carboxylic acid (100 gm) at 25°-35° C. in a dry flask, charge acetone (700 ml) in flask and stir for 10 min. Slowly charge potassium carbonate (168 gm) to reaction mass at 25°-35° C. Add dimethylsulfide (58 ml) slowly to the reaction mass at 25°-35° C. Maintain the reaction mass for 3 hrs at 25°-35° C. Check TLC complies. Filter the salts through celite Hyflo bed. Wash the bed with acetone (100 ml). Distill out acetone ¾ volume of reaction mass at or below 40° C. under vacuum. Cool reaction mass to 25°-35° C. Quench the reaction mass with water (1000 ml) and charge dichloromethane (200 ml) to reaction mass. Stir the reaction mass for 10 min. Settle reaction mass and separate the two layers. Extract the aqueous layer with dichloromethane (150 ml). Combine organic layer wash with water 200 ml 3 times. Dry dichloromethane layer with sodium sulfate. Distill out dichloromethane completely under vacuum below 45° C.-50° C. to get product. Residue weight: 100 gm. (Compound XIII).

Example-6

Charge Vitride® (sodium dihydro-bis-methoxyethoxy aluminate solution in toluene) reducing agent (200 gm) into a dry RBF at 25°-35° C. under nitrogen atmosphere. Cool the Vitride® to 0° C.-5° C. Slowly add toluene (300 ml) into RBF at 0° C.-5° C. Prepare solution of XIII (100 gm) and toluene (200 ml) mixture; add this solution slowly to the reaction mass at 0° C.-5° C. Maintain reaction mass for 10 min at 0° C.-5° C. Raise the temperature to 25° C.-35° C. Maintain the reaction mass for 1 hr at 25° C.-35° C. Check TLC. After TLC complies, cool the reaction mass to 0° C.-5° C. Slowly add saturated ammonium chloride solution to the reaction mass at 0° C.-5° C. Maintain for 10-15 min. at 0° C.-5° C. Filter the salts and wash with toluene (250 ml). Separate the organic layer and aqueous layer. Wash the toluene layer with sodium chloride solution (250 ml×2). Distill toluene out completely under vacuum at or below 70° C. Residue weight: 95 gm. (Compound XIV).

Example-7

Charge MDC (400 ml) into dry RBF. Cool the reaction mass to 0°-5° C. Slowly add oxalyl chloride (150 gm) into the reaction mass at 0° C.-5° C. under nitrogen atmosphere. Stir the reaction mixture at 0° C.-5° C. for 10 minutes. Cool the reaction mass to −60° to −70° C. Add DMSO (135 ml) and MDC (100 ml) solution to reaction mass at −60° to −70° C. Stir for 10 minutes at −65° C. Add compound XIV (100 gm) and MDC (600 ml) solution to reaction mass at −60° to −70° C. Maintain the reaction mass for 30 min at −60° to −70° C. Add triethylamine (420 ml) slowly to the reaction mass at −60° to −70° C. Maintain the reaction mass for 20-30 min at −60° to −70° C. Check TLC. Slowly raise the reaction mass temperature to 25° to 35° C. Quench reaction mass into KH₂SO₄ solution at 25° to 35° C. Stir the reaction mass for 10 minutes. Settle the reaction mass and separate the organic layer. Wash the MDC layer with KH₂SO₄ solution. Dry the MDC layer with sodium sulfate. Distill out the MDC completely under vacuum below 50° C. Residue weight: 80 gm. (Compound XV).

Example-8

Charge compound XV (100 gm) and water (2500 ml) to RBF at 25° to 35° C. Stir for 10 minutes, slowly charge NaHSO₃ (66 gm) into the reaction mass at 25° to 35° C. Stir for 10 minutes, slowly add sodium cyanide (33 gm) into the reaction mass at 25° to 35° C. Stir for 20 minutes at 25° to 35° C. Add (S)-(+)-p-toluenesulfinamide (104 gm) to the reaction mass at 25° to 35° C. Charge methanol (500 ml) to the reaction at 25° to 35° C. Maintain the reaction mass for 1-2 hrs at 25° to 35° C. Slowly raise the reaction mass temperature to 80° to 85° C. Maintain reaction mass for 18 to 20 hrs at 80° to 85° C. Check TLC for compliance. Cool the reaction mass to 25° to 35° C. Charge ethyl acetate (1750 ml) to the reaction mass at 25° to 35° C. Stir for 10 minutes. Separate the layers. Extract aqueous layer with ethyl acetate at 25° to 35° C. Wash ethyl acetate layer with 10% potassium permanganate solution (500 ml×2). Distill out ethyl acetate completely under vacuum at or below 50° C. Residue weight: 130 gm. (Compound XVI).

Example-9

Charge compound XVI (100 gm) into RBF at 25°-35° C. Slowly charge concentrated hydrochloric acid (2100 ml) into RBF at 25°-35° C. Slowly charge acetic acid (500 ml) into RBF at 25°-35° C. Raise the reaction mass temperature to 80°-85° C. Maintain the reaction mass for 16-20 hrs at 80°-85° C. Check TLC for compliance. Distill out 75% of reaction mass under vacuum at or below 80° C. Cool the reaction mass to 25°-35° C. Further cool the reaction mass to 0°-5° C. Maintain the reaction mass 1-2 hrs at 0°-5° C. Filter the reaction mass and wash with chilled water (200 ml). Dry the material at 70°-80° C. Dry weight: 55 gm. (Compound XVII).

Example-10

Charge dimethylformamide (500 ml) and Compound XVII (100 gm) at 25°-35° C. in RBF. Charge phthalic anhydride (65 gm) to reaction mass and stir for 10 minutes at 25°-35° C. Charge potassium carbonate (35 gm) at 25°-35° C. Slowly raise the temperature to 95°-100° C. Maintain the reaction mass for 10-12 hours at 95°-100° C. Check TLC. Filter the salts and wash with 50 ml dimethylformamide. Distill the filtrate thick residue under vacuum at or below 65° C. Charge ethyl acetate (400 ml) to residue at 25°-35° C. Stir for 1 hour at 25°-35° C. Filter the material and wash with ethyl acetate (100 ml). Output: 85 gm. (Compound XVIII).

Example-11

Charge 3% potassium hydroxide solution (1000 ml) and Compound XVIII (100 gm) in RBF at 20°-30° C. Cool the reaction mass to 0°-5° C. Slowly add 200 gm of potassium permanganate (in five lots) at 0° C.-5° C. Maintain the reaction mass for 10 minutes at 0°-5° C. Raise the reaction mass temperature to 20°-25° C. Maintain for 24 hrs at 20°-25° C. Check TLC for compliance. Cool the reaction mass to 0°-5° C. Slowly add sodium bisulphate (100 gm) to the reaction mass at 0°-5° C. Maintain for 30 minutes at 0°-5° C. Filter the salts through Hyflo bed and wash with water (400 ml). Take clear colorless filtrate and cool to 0°-5° C. Charge ethyl acetate (500 ml) to reaction mass at 0°-5° C. Adjust pH with ortho phosphoric acid solution to 2-3 at 0° C.-5° C. Stir for 15 minutes and separate the layers. Extract aqueous layer with ethyl acetate (200 ml). Dry combined organic layer with sodium sulphate (50 gm). Filter the sodium sulphate and wash with ethyl acetate (400 ml). Distill out ethyl acetate completely under vacuum below 60° C. Purify residue by column chromatography. Run the column with 15%-40% ethyl acetate in hexane. Distill the required product fractions under vacuum below 50° C. To residue add hexane (300 ml) for crystallization at 20°-25° C. Filter and wash with isopropyl ether (100 ml). Weight of product: 45 gm. (Compound IIIA).

While the preferred embodiments have been described and illustrated it will be understood that changes in details and obvious undisclosed variations might be made without departing from the spirit and principle of the invention and therefore the scope of the invention is not to be construed as limited to the preferred embodiment.

All references are incorporated by reference herein in their entireties.

REFERENCES

1. Scott A. Savage, Gregory S. Jones, Sergei Kolotuchin, Shelly Ann Ramrattan, True Vu, and Rebert E. Waltermire (2009) Preparation of Saxagliptin, a Novel DPP-IV Inhibitor, Organic Process Research & Development., 13, 1169-1176.
2. Santosh K. Sing, Narendra Manne and Manojit Pal, (2008) Synthesis of (S)-1-(2-chloroacetyl)pyrrolidine-2-carbonitrile: A key intermediate for dipeptidyl peptidase IV inhibitors. Beilstein Journal of Organic Chemistry, 4, No. 20.
3. U.S. Pat. No. (2010) 0274025 A1.
4. U.S. Pat. No. (2006) 0035954 A1.
5. U.S. Pat. No. (2005) 0090539 A1.
6. Organic letters. (2001) Vol. 3, No. 5, Page: 759-762
7. Tetrahedron 59 (2003) 2953-2989

What is claimed is:
1. A method for making

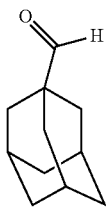

comprising the steps of
treating adamantane 1-carboxylic acid with dimethyl sulfide and potassium carbonate to obtain

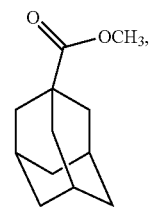

treating the resulting compound with a reducing agent to obtain

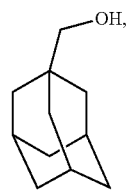

and
treating the resulting compound with triethylamine, dichloromethane, and oxalylchloride.
2. The method according to claim 1 wherein the reducing agent is sodium dihydro-bis-methoxyethoxy aluminate solution in toluene.

* * * * *